United States Patent [19]

Carnaby et al.

[11] Patent Number: 5,727,567
[45] Date of Patent: Mar. 17, 1998

[54] ARTIFICIAL SKIN CONSTRUCTION

[76] Inventors: Ann J. Carnaby, 54 Tide Mill Rd., Hampton, N.H. 03842; Melvin E. Prostkoff, 9 Garrison La., Madbury, N.H. 03820

[21] Appl. No.: 580,452

[22] Filed: Dec. 27, 1995

[51] Int. Cl.$^6$ .................................................. A61F 9/00
[52] U.S. Cl. ................................... 128/857; 602/17
[58] Field of Search ..................... 128/857, 858; 602/17; 623/15

[56] References Cited

U.S. PATENT DOCUMENTS

| | | | |
|---|---|---|---|
| 4,776,324 | 10/1988 | Clarren | 602/17 |
| 5,218,975 | 6/1993 | Prostkoff | 602/17 |
| 5,308,312 | 5/1994 | Pomatto | 602/17 |
| 5,350,583 | 9/1994 | Yoshizato | 623/15 |

OTHER PUBLICATIONS

Larry Nyce, *Water—Modeling with Resin*, Jul./Aug. 1981, pp. 25–29, Mainline Modeler.

Bill Wright, *Odor-free Water*, Fall 1982, pp. 81–82, Model Railroading.

John Nehrich, *Water and how to Model it*, Oct. 1985, pp. 78–81, Model Railroader.

Dave Frary, *How to Build Realistic Model Railroad Scenery*, 1991, Chapter 7, pp. 77–83.

Earl Smallshaw, *Progress report on the Franklin & South Manchester*, Mar. 1990, pp. 88–94, Model Railroader.

Gordon Odegard, *Building Scenery*, 1979, Chapter 5, pp. 39–40, Clinchfield Railroad In N Scale—Model Railroad Handbook No. 13—first appeared in Modern Railroader.

Ed Hammer, Lee Zies, and Marc van Cleven, 1990, Chapter 8, pp. 53–54, Building the Burlington Northern RR in N Scale—Model Railroad Handbook No. 28—first appeared in Modern Railroader.

*Primary Examiner*—Michael A. Brown
*Attorney, Agent, or Firm*—Wolf Greenfield & Sacks P.C.

[57] ABSTRACT

An artificial skin construction for use in overlying a body restorative device to be applied to the body of an individual. The construction provides a cosmetically pleasing skin appearance matched to the skin coloration of the body. The construction has a plurality of see-through layers intermixed with colorant containing layers to provide real life appearance to the artifical skin construction.

10 Claims, 1 Drawing Sheet

ARTIFICIAL SKIN CONSTRUCTION

FIELD OF THE INVENTION

The field of this invention is the provision of cosmetic, aesthetic improvement to restorative devices applied to the body enhance the appearance of such devices.

BACKGROUND OF THE INVENTION

There are many medical conditions where external devices are provided to restore portions of the body, or to support and treat portions of the body. Body restorative devices as used in this application refer to devices such as artificial ears, noses, breasts, limbs and other body parts, cranial prostheses and orthotics such as splints, casts and body plates. In the past, such restorative devices were often used with no cosmetic treatment. Thus, plastics, metals and the like are still exposed to the eye of persons viewing a patient or user. Some of these prostheses are externally worn, outside of normal clothing and can be extremely obtrusive and unpleasant to wear for the users of the devices and unsightly to look at for the persons viewing the user of the device.

Attempts have been made in the past to enhance the appearance of body restorative devices. Often, such attempts are simple attempts to obtain general flesh coloring of some sort and in some cases to simulate the hairy portions of the body. Thus, plastic devices are sometimes colored with one or more colorant in a brownish or pinkish tone. However, oftentimes, this prior art cosmetic treatment of restorative devices falls far short of providing an aesthetically pleasing appearance to the user. The lack of an aesthetically pleasing appearance can have a traumatic emotional effect, particularly in connection with long term wearers of cosmetic devices.

One such prior art restorative device is fully described in U.S. Pat. No. 5,218,975, issued Jun. 15, 1993, entitled cranial prosthesis. This cranial prosthesis is itself a cosmetic device as well as a protective device in that it covers a depression in the skull caused by removal of bone. This is a typical example of a restorative device which could benefit by the teachings of the present invention, which invention can enhance the aesthetics of a cranial prosthesis by provision of an artificial skin construction closely matched to the skin of the wearer of the device.

SUMMARY OF THE INVENTION

It is an object of this invention to provide an artificial skin construction having a plurality of layers which aid in providing a cosmetic appearance which closely matches the skin of the body of a user.

It is another object of this invention to provide a method for forming the artificial skin construction of the preceding object of this invention which method can be carried out in a simplified manner to form cosmetically desirable artificial skin constructions.

Still another object of this invention is to provide a kit containing components useful to form a plural layered construction of a cosmetically pleasing artificial skin in an efficient manner.

According to the invention, an artificial skin construction for use in overlying a body restorative device applied to the body of an individual having a skin coloration, has an outer and an inner surface. The construction comprises a base layer and at least a first and second layer overlying the base layer to form a composite sandwich. The first and second layers each comprise a polymeric material which permits see-through visibility preferably at least to said base layer. At least one of said first and second layers has a predetermined colorant designed to permit interaction of the first and second layers with each other to visually present an artificial skin appearance closely matched to the skin coloration of the individual to which said construction is applied.

Preferably, there are a plurality of additional layers in said construction and at least one or several of said layers are of clear, unpigmented polymeric material to aid in providing depth and three dimensional appearance to the skin construction.

Preferably, the skin construction is mounted directly on a body restorative device and can be formed in place, if desired.

According to the method of this invention, an artificial skin construction for use in overlying a body restorative device applied to the body of an individual having a skin coloration comprises forming a base layer and at least a first and second layer overlying the base layer to form a composite sandwich. The first and second layers are each formed of a coated polymeric material which has see-through properties preferably at least to the base layer. Colorants are incorporated in each of the layers as applied, to interact with each other to visually present an artificial skin appearance closely matched to the skin coloration of the individual to use the construction.

It is a feature of this invention that the method can include the addition of pigments or other colorants to the whole or only portions of each layer. The layers can be discontinuous and/or interrupted along the surface of the artificial skin to provide texturing and/or varying in thickness to provide texturing.

According to the invention, a kit is provided for forming an artificial skin construction. The kit comprises a number of containers, each having a castable polymeric material with at least some of said polymeric materials carrying colorants to enable coating of the materials with interaction of successive overlying layers formed, from said plurality of packages of materials, to form a three-dimensional skin colored artificial skin material as a sandwich of coated layers, or a single container of castable polymeric material and several containers of varying colorants to be added to the castable polymeric at the time the artificial skin is constructed.

it is a feature of this invention that the artificial skin can be provided with a surface texture to simulate natural skin of the body, pigmentation, body blemishes and the like which can be simulated by placement of colorants, pigments and the like in various layers, as desired, and three-dimensional effect can be obtained by the use of clear layers or clear or colored portions of layers used. It is another feature of this invention that the layers can be discontinuous and/or interrupted along the surface of the artificial skin to provide texturing and/or varying in thickness, as in the formation of skin wrinkles and furrows. It is another feature of this invention that a sandwich formed of the various layers can have a mechanically strong base which can be adhered to a body restorative device or the polymeric layers can themselves be directly adhered and in some cases formed on a polymeric device.

BRIEF DESCRIPTION OF THE DRAWINGS

The above and other features, advantages and objects of the present invention will be better understood from a

Figure 1:
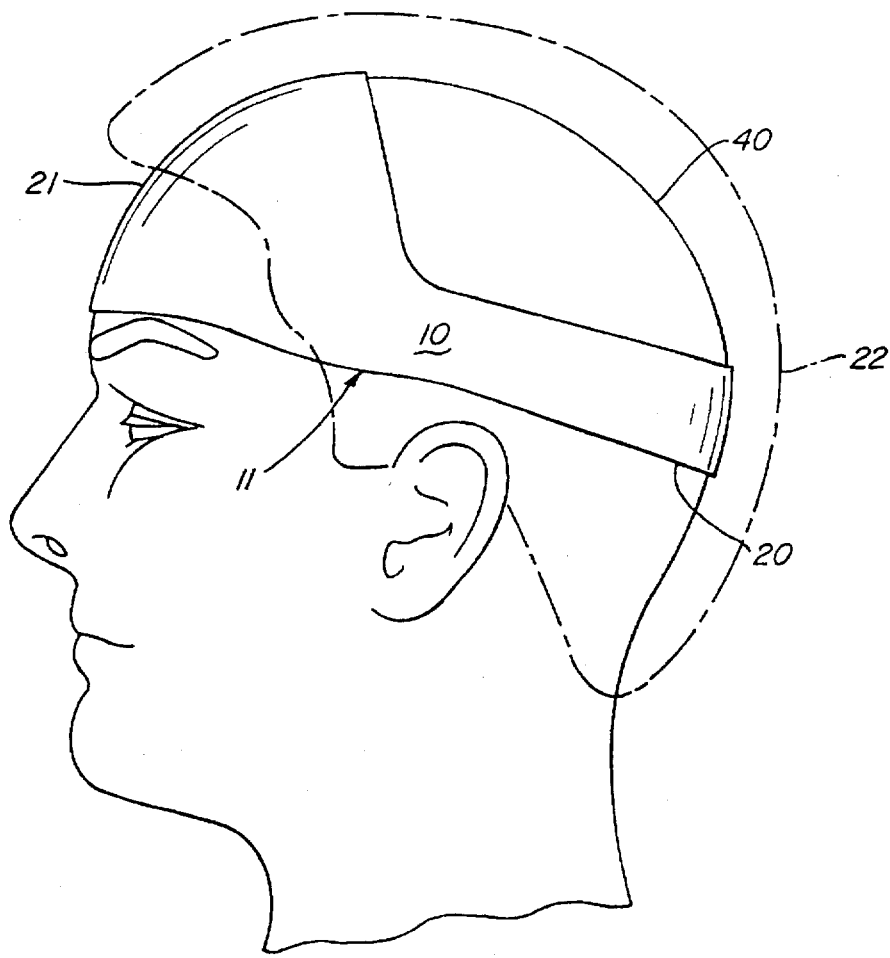
Figure 2:
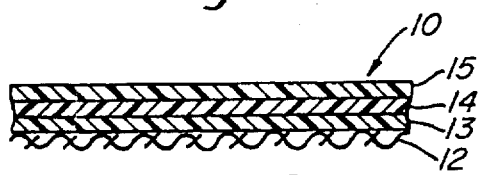
Figure 3:
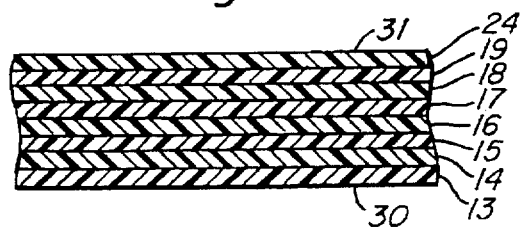
Figure 4:

3 reading of the following specification in conjunction with the accompanying drawings in which:

FIG. 1 is a side view of a restorative device in accordance with the prior art having applied thereto an artificial skin construction in accordance with the present invention, FIG. 2 is a cross section view through the preferred embodiment of the artificial skin construction as shown in FIG. 1, covering the restorative device, FIG. 3 is a cross-sectional view through an alternate embodiment of this invention; and FIG. 4 is a cross-sectional view through another alternate embodiment of this invention.

DESCRIPTION OF THE PREFERRED EMBODIMENT

With reference now to the drawings, a preferred embodiment of the present invention is illustrated at 10 in FIG. 1 and FIG. 2. The artificial skin construction 10 is applied over a cranial prosthesis 11 and the artificial skin construction has a base layer 12 and a plurality of additional layers forming the sandwich of the construction 10 which additional layers are denoted in FIG. 2 at 13, 14 and 15.

The cranial prosthesis 11 is constructed in accordance with that shown in U.S. Pat. No. 5,218,975, dated Jun. 15, 1993 entitled cranial prosthesis, which patent is incorporated by reference herein. The prosthesis 11 is formed of a hard plastic material and is applied over a portion of the skull where a cranial bone is removed or absent, so as to cover depression in the skull. However, it should be understood that the artificial skin constructions of the present invention can be used to cover or be attached to any body restorative device including orthotic devices of all types such as artificial ears, noses, breasts and splints, artificial limbs, body plates, cranial prosthesis, and the like. In all cases, it is preferred that the artificial skin construction be colored to closely match the skin color of the body of the user at or near the location where the restorative device is used.

For example, in the cranial prosthesis 11 shown mounted on the skull of a person 40, there is a band portion denoted by the bottom line 20 of the prosthesis 11, which extends around the head and a cranial depression covering portion 21 at the forehead and upper portion of the skull. The forehead portion is colored by the artificial skin construction 10 to closely match the skin of the forehead. The band portion of the artificial construction which is over the normal hair section, could have hair applied to it to simulate the hair of the user. In some cases, a wig shown in the dotted outline at 22 can be used over a portion of the skin construction 10. The artificial skin construction 10 of the preferred embodiment is preferably adhered to the prosthesis 11 by the use of a latex adhesive or other attachment means which could be physical attachment means such as clips and the like, or mechanical attachment means such as heat bonding with a low temperature heat gun or other means.

Turning now to FIG. 2, a cross-section through the artificial skin construction 10 is illustrated. The base layer 12 in this embodiment is a mechanically strong base layer which provides mechanical integrity to the artificial skin construction. The construction 10 is in the form of a sandwich shown with each of the layers adhered to each other. The layer 12 can be a conventional cotton fabric or elasticized material, plastic or any other material desired which provides a support base. In some cases, layer 12 need not be used, but the sandwich can be composed of polymeric materials alone, with the lowermost polymeric layer acting as a base layer, if desired.

4

The polymeric materials of layer 13, 14 and 15 are preferably formed of the same material applied in a casting or coating technique to form thin layers. In some cases, the layers can be formed of different polymeric materials.

Latex or silicone rubbers are preferred for use for the polymeric material of the layers 13, 14 and 15. Silastic brand latex, which is a silicone rubber latex produced by Dow Corning of Midland, Mich., can be used as the polymeric material of this invention. However, other rubber latex and polymeric materials such as urethanes and the like can be used if desired. Silicone rubber, natural rubber latex, or other synthetic elastomers are preferred, since they are readily available and approved by the FDA for various medical devices.

The rubber latex materials, as known, can be cast or coated and dried in a succession of layers which adhere to each other, each of which can carry various colorants and/or be clear, that is, transparent or translucent. Preferably, elastomeric layers are used particularly where the artificial skin construction is not formed directly on a rigid surface such as a prosthetic.

Often, the constructions are used with a cloth base, as in the preferred embodiment, although in some cases, the skin constructions can be formed as shown in FIG. 4 with a plurality of sandwiched silicone and/or latex rubber or other polymeric material layers 13, 14, 15 without the fabric base.

In all cases, resiliency of the material is preferred to enable fitting on and in some cases stretching or conformance of the artificial skin to an underlying prosthetic for attachment thereto or use therewith. When no physical or adhesive attachment is used, the inherent resiliency of the artificial skin construction can be used to hold the construction in place on the prosthetic. Thus, the base 12 or polymeric layer 13 which acts as a base can be adhesively bound to an underlying restorative device such as 11.

Although the preferred embodiment of FIG. 2 shows three layers or coatings above the fabric, in some cases, only three layers of polymeric material can be used as shown in the embodiment of FIG. 4. In other cases, many layers can be used as shown in FIG. 3.

In another preferred embodiment, 8 to 10 distinct layers are employed, sandwiched together and formed by coating methods as will be described. The number of layers can be varied as desired. In FIG. 3, eight polymeric layers are used, i.e., 13–19 and 24 extending from an inner surface 30 to an outer surface 31. In some cases, the number of layers will depend upon the type of skin being replicated, i.e. older, more textured skin often requires more layers than younger, smoother skin to obtain a desired cosmetic effect. In other cases, greater depth and three-dimensional effect can be obtained by using a plurality of clear layers interspersed between layers containing colorants and the like.

Each of the latex layers, or at least two of the latex layers can have incorporated colorants of various types. Colorants suitable for use in the present invention to enable achieving a cosmetic effect are preferably FDA approved cosmetic pigments. Pigments such as red, blue, various shades of these colors including light, medium and dark flesh pigments, brown, brick red and mustard yellow, are among those that are useful in the various layers. Such colorants for use in medical grade latex, as for example, medical grade latex obtained from Heaveatex Corp. of Fall River, Mass. are useful in this invention.

Useful colorants further include cosmetic russet (iron oxide) obtained from Sun Chemical Corporation of Cincinnati, Ohio; cosmetic brown, obtained from Sun Chemical Incorporated; cosmetic turquoise, number 7018, obtained from Clark Colors Incorporated of Plainfield, N.J.; red iron oxide, obtained from Clark Colors Incorporated; D & C Yellow No. 5, obtained from Clark Colors Incorporated; magnesium carbonate, obtained from Whittaker, Clark and Daniels; black B.C., obtained from Hilton Davis of Cincinnati, Ohio; ultra rose B.C., obtained from Hilton Davis of Cincinnati, Ohio; titanium oxide, obtained from Whittaker, Clark and Daniels, inc. of Plainfield, N.J. Talc and zirconium lake orange pigment are particularly useful in this invention, although others can be used.

Suitable adhesives for adhering the artificial skin construction to a restorative device include Pros-Aide adhesive, an acrylic latex emulsion produced by ADM Tronics of Northvale, N.J. Such adhesives can be used to adhere the artificial skin construction 10 to the prosthetic, or in some cases to adhere the edge or a portion of the skin construction directly to the skin to provide continuity of appearance.

As noted above, each of the layers 13-19 and 24 and other similar layers if desired can be employed coated seriatim on a base such as 12 or applied to a restorative device surface by a coating or casting technique. When latex or silicone rubber is used, a thin layer is applied and dried, and additional layers are applied and dried one at a time to form a skin construction. These layers form a sandwich adhered to each other.

Preferably in the method of this invention, a casting or coating technique is used. This can be done for example by an individual using a hand brush to paint a thin coating on an underlying surface. Preferably the layer thickness of each layer as applied and dried is in the range of about from 0.001 to about 0.005 inch, with a preferred composite or total thickness of the sandwich of from 0.032 inch to about 0.045 inch. Total sandwich thicknesses of less than 0.1 inch or less are preferred for use. Although the layers are approximately of equal thickness, this need not be the case. The layers can vary in thickness and can be applied over the whole or only a portion of an underlying layer.

In some cases, surface texturing can be obtained by using layers which are discontinuous, that is do not entirely cover the underlying layer. This can provide surface texturing at the outer surface of the skin construction or thereunder such as when forming wrinkles and furrows and raised and depressed blemishes or moles, and the like. Thus, a series of textures at the surface can be provided by discontinuity in one or more of the layers or portions of the layers.

In addition to the colorants used in proper combination, close simulation to the skin of a selected individual with which the artificial skin construction is to be used, can be obtained by applying colorants to act as artificial surface or skin blemishes. Warts, moles, rashes, skin markings can be simulated. For example, a portion of a layer can have a dark brown spot to simulate a discolored portion as might appear in an age spot in the skin of an individual. One or more layers may be combined to produce a skin spot or aging spot effect in the skin. Similarly, warts can be simulated by buildup of generally circular layers at portions of the skin construction.

Hair can be used and adhered to the latex. Artificial hair or human hair, either as individual hair fibers or as a collective preconstructed hairpiece can be applied to the latex as it dries to give a hair covering as may be useful in connection with the cranial prosthesis.

It is an important feature of the present invention that close simulation of the skin of the particular user can be obtained by mixing various colorants, one or more in each layer to obtain an overall three-dimensional effect. Since the layers are "see-through" at least in part, that is, transparent or translucent, even though carrying a uniform or non-uniform colorant throughout or a colorant only at selected portions, a three-dimensional effect is obtained by a plurality of layers of this type.

A kit useful for carrying out the method of this invention can be preassembled so as to enable a user to put together an artificial skin construction to closely simulate any particular user's skin. Such a kit has a plurality of packages which can be plastic, glass vials or the like, some containing a polymeric material such as latex rubber. Preferably, at least one of the vials is a clear, unpigmented latex rubber or other polymeric material, and each of the other vials preferably have a different colorant to give a variety of combinations. For example, a package of a paintable, coating latex can comprise vials having the following combination of colors: light flesh, tan, medium flesh, darker tan, dark flesh, darker tan, ruddy flesh, red tan, brick red colorant, brown colorant, mustard yellow colorant, blue colorant, bright red colorant, mixed orangy pigments, mustard yellow color, brown and mustard yellow, medium flesh ruddy color, and others if desired. There may also be one vial containing clear, paintable coating latex, and others containing the individual pigments not yet mixed with the polymeric material.

Such a kit may also preferably comprise a measuring spoon such as to measure dry pigment if the individual pigment is to be mixed with the latex and a brush for use in applying the mixed latex and clear latex in the method of this invention.

By using the method of this invention, the artificial skin construction can be designed to have thickness, color and surface texture to closely simulate the skin of the body of the user for whom the skin is intended.

The variety of pigments and colorants which are useful in a plurality of layers as opposed to a single layer colorant as often used in the prior art, enables one to duplicate the skin colorants which come from melanocytes, blood and other feature of the skin. These skin colorants give a different appearance to the skin of various individuals. The use of a plurality of layers, each containing different colorants interspersed with clear layers as in the present invention, can come closer than hithertofore done in obtaining the desired flesh matching effect.

Several colors or pigments can be added to the artificial skin construction to simulate the various colors present in the human skin and the colors and pigments can be placed at different depths of the artificial skin to give a three-dimensional effect corresponding to the depths at which similar colors are located in human skin. Because see-through or clear layers are used interspersed with pigmented or colored layers, a three-dimensional effect is obtained.

In the method of this invention, the artificial skin construction is made by building up layers of soft and supple medical grade latex over a fabric or over each other. The resulting artificial skin construction is then attached to a prosthetic or orthotic. In some cases, the coated layer can be coated directly on the restorative device or to a base fabric layer attached thereto. A lifelike appearance can be obtained particularly in view of the depth resulting from the sandwich or laminate. The see-through properties in conjunction with plural layers, allow variation in appearance to the eye at different depths.

Texture can also be created by applying latex thicker at some portions as where a wart, mole or vein is to be simulated and thinner where there is an absence of skin as in a crease, furrow, or a wrinkle. Surface texture simulating the fine network of wrinkles found in older or very dry skin can be constructed by dabbing on the top of the layer of latex with a cotton swab.

In a particular embodiment of using the present invention, the following supplies are used: a No. 8 round brush, a No. 00 brush, liquid soap, measuring spoons, cotton swabs. Overall the following technique is employed.

Each layer of latex must dry before adding the next. Drying may be quickened by using a low temperature heat gun such as a hair dryer at a low temperature.

The No. 8 round brush is immersed in soapy water when not applying latex to thoroughly cleanse it in between applications and to prevent buildup of latex on the bristle brush. The latex packages used of the various colorants as described above, are kept covered so as to prevent hardening within the jar or container due to exposure to room air.

In the preferred embodiment, a fabric layer of a cotton cloth is first formed over a cranial prosthesis such as 11. A bonding adhesive which is a medical adhesive such as Silastic brand (medical adhesive type A catalog No. 891, available from Dow Corning of Midland, Mich.) is painted on an underlying plastic cranial prosthesis as shown at 11 and a fabric cotton cloth layer 12 is then adhered over the cranial prosthesis as shown at 11 and cut to the shape of the prosthesis or the cloth is mechanically bonded to the prosthesis with heat. The cloth encircles the head and covers the cranial prosthesis 11 to its edges.

From this point on, the latex layers are applied by a brushing technique. A clear latex layers are applied by a pigment color of skin colors to be used is applied by brushing with a No. 8 round brush (a cotton swab may be used). For example, one part pigment to three parts water by volume can be used, mixed with 1–5 parts by volume latex that is obtained from a company such as Heveatex Corp. as is the case with most pigments used. The single layer is applied as are all layers in this embodiment at a thickness of 0.003 inches although this can vary within the range of 0.001 to about 0.005 inches dry thickness. After each layer is applied, it is dried with a hair dryer at a low heat setting, although it can be air dried at room temperature.

It is hard to be exactly uniform in thickness since brushing techniques are used and there is often variation in the thickness of each layer. In this pigmented layer, as in all pigmented layers, the clear latex is that obtained from a company such as Heveatex Corp. to which has been added one part pigment and three parts water intermixed therewith to give a color.

In the first layer 13 as shown in FIG. 4, the darkest color is at the lowest layer and the pigmented layers get lighter towards the outer surface of the device. In the first lower layer 13, for example, one part blue (ultramarine blue, available from Bob Kelly Cosmetics Inc., New York, N.Y.) coloring and three parts by volume clear natural rubber latex are intermixed and then applied. Subsequent layers 14 and 15 are then applied. The sequence of various colored layers is as follows: layer 13 (blue), layer 14 (clear), layer 15 (medium flesh).

Layer 14 is preferably a clear natural rubber latex without color or any pigment.

Layer 15 is a clear, natural rubber latex which has uniformly admixed therein medium flesh pigment comprised of titanium dioxide, talc and iron oxide available from Bob Kelly Cosmetics, Inc., New York, N.Y. in any amounts of one part pigment by volume to three parts latex.

Each layer is applied, dried and then the next layer applied. The overall skin construction of FIG. 4 results which can match a light skin of an individual.

In preferred embodiments, 8 to 25 layers of latex are used in order to better obtain a variation in color over the surface of the artificial skin construction.

In the 8 layer embodiment, the numbered layers are from a kit of packages of mixed or separate latex and pigment, each containing materials noted for each layer, as follows:

1. red and blue pigment in latex
2. clear latex
3. darkest skin tone selected in latex, e.g.: dark flesh
4. clear latex
5. medium tone selected in latex, e.g.: light ruddy
6. clear latex
7. light tone selected in latex, e.g.: light flesh
8. clear latex While specific embodiments of this invention have been shown and described, it will be obvious that many modifications can be used. It is important that at least three or more layers and preferably from 8 to 25 layers of a clear latex be used with at least some of the layers having colorants either uniformly dispersed therein or dispersed at different portions thereof to provide a desired overall three-dimensional effect. It is an advantage of this invention that a preset kit, having latex or other polymeric material carriers in packages be used with at least one clear unpigmented, uncolored package and various colors in other packages to enable various combinations of layers to be applied to the artificial skin construction.

What is claimed is:

1. A cosmetic artificial skin construction for use in overlying a body restorative device applied to the body of an individual, said construction having a skin coloration, said construction having an outer surface and an inner surface and comprising a base layer with at least a first and second layer overlying said base layer to form a composite sandwich, said first and second layers each comprising a polymeric material which permits see-through visibility at least to said base layer, at least one of said first and second layers having a predetermined colorant designed to permit interaction of said first and second layers with each other to visually present an artificial skin appearance closely matched to the skin coloration of said individual which said construction is applied.

2. A costmetic artificial skin construction in accordance with claim 1, wherein at least one of said layers comprises at least one clear, unpigmented portion.

3. A cosmetic artificial skin construction in accordance with claim 2, wherein at least said outer surface of said construction is textured to simulate normal skin.

4. A cosmetic artificial skin construction in accordance with claim 2 and further comprising said base layer having mechanical properties to support said first and second layers and act as a means for mounting said artificial skin construction on the body restorative device attached thereto.

5. A cosmetic artificial skin construction in accordance with claim 4 and further comprising a body restorative device attached to said base layer.

6. A cosmetic artificial skin construction in accordance with claim 2 and further comprising at least five layers constructed in accordance with said first and second layers, said layers each having an overall thickness of approximately 0.001 to about 0.005 inch, with a total sandwich thickness of no greater than 0.1 inch.

7. A cosmetic artificial skin construction in accordance with claim 6, wherein said layers generally vary in darker coloration with the lightest coloration at said outer surface and the darker colorations extending towards said inner surface.

8. A cosmetic artificial skin construction in accordance with claim 7 wherein at least two of said layers are clear to enhance three dimensional effect of said skin construction.

9. A method of forming cosmetic artificial skin construction for use in overlying a body restorative device which can be applied to the body of an individual having a skin coloration, said method comprising forming a base layer and depositing successive layers of a polymeric material thereover, said polymeric material comprising materials selected from colorant containing and non-colorant containing material to impart see-through visibility to said layers so deposited, said colorants designed to permit interaction among said layers to visually present an artificial skin appearance closely matched to the skin coloration of the individuals to which the constructions are applied.

10. A kit for use in forming a cosmetic artificial skin construction, said kit comprising, a plurality of polymeric coating materials having preselected different colorants each of said different colorants being selectable to mimic a skin appearance, a clear polymeric coating material being devoid of colorant, said colorant containing polymeric materials being selected to allow interaction with each other to provide for a wide variety of natural skin colorants when certain of said coating materials are coated in a sandwich configuration.

* * * * *